US012678379B2

(12) United States Patent
Kawana et al.

(10) Patent No.: US 12,678,379 B2
(45) Date of Patent: Jul. 14, 2026

(54) PASTE-LIKE COMPOSITION FOR DENTAL USE, AND METHOD FOR PRODUCING THE SAME

(71) Applicant: KURARAY NORITAKE DENTAL INC., Kurashiki (JP)

(72) Inventors: Mariko Kawana, Niigata (JP); Nobusuke Kashiki, Aichi (JP)

(73) Assignee: KURARAY NORITAKE DENTAL INC., Kurashiki (JP)

( * ) Notice: Subject to any disclaimer, the term of this patent is extended or adjusted under 35 U.S.C. 154(b) by 981 days.

(21) Appl. No.: 17/789,264

(22) PCT Filed: Dec. 26, 2020

(86) PCT No.: PCT/JP2020/049052

§ 371 (c)(1),
(2) Date: Jun. 27, 2022

(87) PCT Pub. No.: WO2021/132707

PCT Pub. Date: Jul. 1, 2021

(65) Prior Publication Data

US 2023/0049373 A1 Feb. 16, 2023

(30) Foreign Application Priority Data

Dec. 27, 2019 (JP) ................................ 2019-239878

(51) Int. Cl.

*A61K 6/71* (2020.01)
*A61K 6/15* (2020.01)
*A61K 6/30* (2020.01)

(52) U.S. Cl.

CPC .................. *A61K 6/71* (2020.01); *A61K 6/15* (2020.01); *A61K 6/30* (2020.01)

(58) Field of Classification Search

CPC ........................................................ A61K 6/71
See application file for complete search history.

(56) References Cited

U.S. PATENT DOCUMENTS

| | | | | |
|---|---|---|---|---|
| 4,719,297 | A | 1/1988 | Henne et al. | |
| 2011/0257292 | A1* | 10/2011 | Okubayashi | A61K 6/69 523/115 |
| 2013/0172441 | A1 | 7/2013 | Takahata et al. | |
| 2015/0320646 | A1* | 11/2015 | Kameya | A61K 6/887 433/90 |
| 2016/0030296 | A1 | 2/2016 | Kadobayashi et al. | |
| 2021/0015716 | A1 | 1/2021 | Hong et al. | |

FOREIGN PATENT DOCUMENTS

| | | | |
|---|---|---|---|
| EP | 2926796 | A1 | 10/2015 |
| JP | H03-57916 | B2 | 9/1991 |
| JP | H09-194674 | A | 7/1997 |
| JP | H10-306008 | A | 11/1998 |
| JP | 2016030740 | A | 3/2016 |
| JP | 2018145133 | A | 9/2018 |
| WO | WO-2011074222 | A1 | 6/2011 |
| WO | WO-2012042911 | A1 | 4/2012 |
| WO | WO-2019124515 | A1 | 6/2019 |

OTHER PUBLICATIONS

International Search Report issued Feb. 16, 2021 in PCT/JP2020/049052 (with English translation), 4 pages.
Extended European Search Report issued Dec. 20, 2023 in corresponding European Patent Application No. 20905728.0, 8 pages.

* cited by examiner

*Primary Examiner* — Michael F Pepitone
(74) *Attorney, Agent, or Firm* — Element IP, PLC

(57) ABSTRACT

The present invention provides a paste-like composition for dental use that shows stable consistency and runniness and little stringiness immediately after production and even after long storage. The present invention relates to a paste-like composition for dental use, comprising a polymerizable monomer (A) and a filler (B), the filler (B) comprising a particulate filler (B-1) having an average primary particle diameter of 0.001 to 0.2 μm, and a filler (B-2) having an average primary particle diameter of more than 0.2 μm and 30 μm or less, the paste-like composition having a consistency of 15 to 40 mm, the particulate filler (B-1) having an average secondary particle diameter of 20 μm or less.

11 Claims, No Drawings

PASTE-LIKE COMPOSITION FOR DENTAL USE, AND METHOD FOR PRODUCING THE SAME

CROSS REFERENCE TO RELATED APPLICATIONS

This application is a 371 of PCT/JP2020/049052 filed Dec. 26, 2020, and claims priority to Japanese application 2019-239878 flied Dec. 27, 2019.

TECHNICAL FIELD

The present invention relates to a paste-like composition for dental use used for filling or prosthetic restoration of tooth defects in the field of dentistry, and to a method of production of such a paste-like composition.

BACKGROUND ART

Adhesive materials and restorative filling materials are widely used for the restorative treatment of tooth defects caused by damage such as caries and fractures. The type of adhesive material or restorative filling material that is in common use for tooth restoration is a resin curable composition composed of materials such as a radical polymerizable monomer, a polymerization initiator, and a filler.

The resin curable composition used for direct restoration, or a material used with a dental bonding agent to fill tooth defects, is called dental filling composite resin, whereas dental resin cement is a term used to refer to materials used for indirect restoration, that is, bonding of a prosthesis to tooth structure. A restorative treatment of deep caries reaching the tooth pulp requires removal of the tooth pulp and construction of an abutment tooth. Materials used for this purpose are called dental composite resin for abutment construction. The dental filling composite resin, dental resin cement, and dental composite resin for abutment construction are all paste-like compositions. As a rule, these paste-like dental compositions are produced by mixing a powdery filler with a liquid-form polymerizable-monomer-containing composition dissolving components such as a polymerizable monomer, a polymerization initiator, an accelerator, and a stabilizer, and are delivered to the user, dentists, after being filled in a packaging container.

The paste properties of paste-like compositions for dental use such as dental filling composite resins, dental resin cements, and dental composite resins for abutment construction are evaluated using indices such as consistency, stringiness, runniness, ejectability, stickiness, and separation. The paste properties are adjusted according to the intended use of these materials and their applications.

For example, dental filling composite resins have two categories: a universal filling composite resin with reduced runniness that uses filling instruments for filling, and a flowable filling composite resin that is directly flowable into a cavity from a container such as a syringe. Because these are used to fill cavities, the both resins are required to have paste properties with little stringiness or stickiness, despite different degrees of paste flowability.

The dental resin cement, a material used to bond a prosthesis, requires moderate flowability because the paste, when too hard, causes problems such as elevation in applying a prosthesis to a tooth. The dental resin cement also requires moderate formability because removal of excess cement—a portion of cement protruding from the prosthesis and that needs to be removed after bonding—becomes difficult when the paste has high runniness and the excess cement spreads around the prosthesis and the tooth margin of the tooth structure.

The dental composite resin for abutment construction requires moderate flowability to be able to flow into the root canal when used with the direct method—a process that directly fills the composite resin into the root canal inside the oral cavity for build-up of an abutment tooth. At the same time, the dental composite resin for abutment construction needs to have moderate formability because it is also used to build an abutment tooth.

The dental filling composite resin is typically a one-paste light-cure resin composition, whereas the dental resin cement and the dental composite resin for abutment construction are often available as either one-paste light-cure compositions or two-paste dual- or chemical-cure compositions. The two-paste dual- or chemical-cure material is either auto-mixing, where the material is taken with an installed automatic mixing tip, or hand-mixing, where the pastes are hand-mixed on mixing paper by an operator using a tool such as a mixing spatula. Auto-mixing requires the pastes to be extruded with a light force, whereas even better ease of mixing is required for pastes mixed by hand.

In all of these paste-like compositions, the paste properties must remain stable throughout the shelf life of the product, and always provide the same level of usability for dentists and hygienists. The shelf life of paste-like compositions for dental use such as dental filling composite resins, dental resin cements, and dental composite resins for abutment construction is typically about 2 to 4 years. It is, however, difficult for the composition to maintain stable paste properties throughout the duration of its shelf life, and the paste properties often change with time after production, bringing the product out of its optimum range for intended use.

It is commonly believed that the particle diameter, shape, and content of inorganic fillers are the major factors that have the greatest impact on the paste properties of a paste-like composition for dental use. For example, a paste-like composition for dental use containing a relatively large amount of irregularly shaped inorganic fillers having an average primary particle diameter of 0.2 μm or more is not easily formable, and tends to be runny, though such paste-like compositions are high in mechanical strength. On the other hand, a paste-like composition for dental use containing a relatively large amount of inorganic fillers having an average primary particle diameter of 0.2 μm or less tends to suffer from poor ease of handling because of increased viscosity, though runniness improves. Increasing the content of inorganic filler to obtain high mechanical strength often results in a hard paste, whereas decreased inorganic filler contents tend to impair ease of handling by seriously increasing paste stickiness or runniness, in addition to decreasing mechanical strength.

As a means of obtaining desirable paste properties in a paste-like composition for dental use, Patent Literature 1 discloses a method that reduces paste runniness by containing an aggregate of inorganic fine particles having a specific particle size distribution.

Patent Literature 2 discloses a process of producing a paste having stable properties. Specifically, Patent Literature 2 discloses conditions, such as mixing time and temperature, needed to achieve stable paste properties, in connection with a mixed polymerizable monomer fabrication step, a sliane treatment step for filler, a composite material production step of mixing a polymerizable monomer and a filler, and a filling step.

CITATION LIST

Patent Literature

Patent Literature 1: JP H10-306008 A
Patent Literature 2: JP 2016-030740 A

SUMMARY OF INVENTION

Technical Problem

However, Patent Literature 1 does not describe anything about the stability of paste properties over the long term. Patent Literature 2 does not specify amounts or procedures for adding the polymerizable monomer in the composite material production step. In Patent Literature 2, the stability of paste properties is confirmed by evaluating flowability and extrudability for the paste properties of a one-paste composition. However, in actual practice, runniness or stringiness may change even when flowability or extrudability is stable. Patent Literature 2 does not describe anything about two-paste composition. Stable paste properties are more difficult to achieve in two-paste compositions than in one-paste compositions because the factors involved in changes of paste extrudability and kneadability are more complex in two-paste compositions. Patent Literature 2 is also silent about mechanical strength, a quality associated with dispersibility of fillers.

It is accordingly an object of the present invention to provide a paste-like composition for dental use that shows stable consistency and runniness and little stringiness immediately after production and even after long storage. Another object of the present invention is to provide a method of production of such a paste-like composition.

Solution to Problem

The present inventors conducted intensive studies to achieve the foregoing objects, and found that the above issues can be solved when a paste-like composition for dental use containing two types of fillers, large and small, having specific average primary particle diameters has a specific range of average secondary particle diameter for the filler having a smaller average primary particle diameter, and a specific range of paste consistency. Specifically, in a method that produces a paste-like composition for dental use, a liquid composition containing a polymerizable monomer is kneaded with a filler in such a fashion that an intermediate paste is first produced by kneading a composition containing a portion of the polymerizable monomer-containing composition, and a particulate filler having an average primary particle diameter of 0.001 to 0.2 μm. Here, because the polymerizable monomer and the particulate filler used for kneading produce a hard paste, the particulate filler can be thoroughly dispersed in the intermediate paste. In producing the intermediate paste, it is preferable not to introduce all the polymerizable monomer-containing composition in the first stage of kneading. The average secondary particle diameter of the particulate filler can be controlled, and the paste consistency can be confined within a specific range by kneading the remaining part of polymerizable monomer-containing composition with a filler having an average primary particle diameter of 0.2 μm to 30 μm after optionally introducing these components to the intermediate paste in a stepwise fashion. A paste having the specific ranges of average primary particle diameter and average secondary particle diameter, and the specific range of consistency was found to show stable paste properties over the long term. In certain embodiments, the specified state of filler dispersion was found to be highly effective also for mechanical strength and marginal sealing of a paste-like composition for dental use. The present invention was completed after further studies.

Specifically, the present invention includes the following.

[1] A paste-like composition for dental use, comprising a polymerizable monomer (A) and a filler (B),
 the filler (B) comprising a particulate filler (B-1) having an average primary particle diameter of 0.001 to 0.2 μm, and a filler (B-2) having an average primary particle diameter of more than 0.2 μm and 30 μm or less,
 the paste-like composition having a consistency of 15 to 40 mm,
 the particulate filler (B-1) having an average secondary particle diameter of 20 μm or less.

[2] A method for producing a paste-like composition for dental use that comprises a polymerizable monomer (A) and a filler (B), and in which the filler (B) comprises a particulate filler (B-1) having an average primary particle diameter of 0.001 to 0.2 μm, comprising the steps of:
 mixing the polymerizable monomer (A) and the particulate filler (B-1) having an average primary particle diameter of 0.001 to 0.2 μm to obtain an intermediate paste; and
 additionally mixing the polymerizable monomer (A) with the intermediate paste to obtain a final paste as a paste-like composition for dental use,
 the particulate filler (B-1) in the step of obtaining an intermediate paste being mixed in an amount of 30 to 150 parts by mass relative to total 100 parts by mass of the polymerizable monomer (A).

[3] The method for producing a paste-like composition for dental use according to [2], wherein the particulate filler (B-1) contained in the final paste has an average secondary particle diameter of 20 μm or less.

[4] The method for producing a paste-like composition for dental use according to [2] or [3], wherein the intermediate paste has a consistency of 5 to 20 mm.

[5] The method for producing a paste-like composition for dental use according to any one of [2] to [4], wherein the particulate filler (B-1) contained in the intermediate paste has an average secondary particle diameter of 100 μm or less.

[6] The method for producing a paste-like composition for dental use according to any one of [2] to [5], wherein the paste-like composition for dental use comprises a filler (B-2) having an average primary particle diameter of more than 0.2 μm and 30 μm or less.

[7] The method for producing a paste-like composition for dental use according to [6], wherein the filler (B-2) is mixed in the step of obtaining an intermediate paste.

[8] The method for producing a paste-like composition for dental use according to [6] or [7], wherein the filler (B-2) is mixed in the step of obtaining a final paste.

[9] The method for producing a paste-like composition for dental use according to any one of [2] to [7], wherein the particulate filler (B-1) is not added to the intermediate paste in the step of obtaining a final paste.

Advantageous Effects of Invention

A paste-like composition for dental use of the present invention has excellent effects with stable consistency and runniness and little stringiness, immediately after production and even after long storage. According to the present invention, a paste-like composition for dental use can be provided that also excels in mechanical strength and marginal sealing. The present invention can also provide a method of production of such a paste-like composition.

DESCRIPTION OF EMBODIMENTS

A paste-like composition for dental use of the present invention comprises a polymerizable monomer (A). Examples of the polymerizable monomer (A) include a polymerizable monomer having an acidic group, and a polymerizable monomer having no acidic group. The polymerizable monomer may be used alone, or two or more thereof may be used in combination.

Examples of the polymerizable monomer having an acidic group include polymerizable monomers having at least one acidic group such as a phosphoric acid group, a pyrophosphoric acid group, a thiophosphoric acid group, a phosphonic acid group, a sulfonic acid group, and a carboxylic acid group, and at least one polymerizable group such as an acryloyl group, a methacryloyl group, a vinyl group, and a styrene group. The polymerizable monomer having an acidic group has affinity for adherends, and shows demineralizing effect on tooth structure. In view of polymerizability, the acidic group-containing polymerizable monomer preferably has an acryloyl group or a methacryloyl group as a polymerizable group. In view of biosafety, the acidic group-containing polymerizable monomer more preferably has a methacryloyl group. Specific examples of the polymerizable monomer having an acidic group are as follows. In the following, "(meth)acryl" is a collective term for methacryl and acryl. The same applies to similar expressions such as "(meth)acryloyl".

Examples of polymerizable monomers having an phosphoric acid group include 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-acryloyloxydecyl dihydrogen phosphate, 10-methacryloyloxydecyl dihydrogen phosphate (hereinafter, also referred to in an abbreviated form as "MDP"), 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyeicosyl dihydrogen phosphate, bis[2-(meth)acryloyloxyethyl]hydrogen phosphate, bis[4-(meth)acryloyloxybutyl]hydrogen phosphate, bis[6-(meth)acryloyloxyhexyl]hydrogen phosphate, bis[8-(meth)acryloyloxyoctyl]hydrogen phosphate, bis[9-(meth)acryloyloxynonyl]hydrogen phosphate, bis[10-(meth)acryloyloxydecyl]hydrogen phosphate, 1,3-di(meth)acryloyloxypropyl dihydrogen phosphate, 2-(meth)acryloyloxyethylphenyl hydrogen phosphate, 2-(meth)acryloyloxyethyl-2-bromoethyl hydrogen phosphate, bis[2-(meth)acryloyloxy-(1-hydroxymethyl)ethyl]hydrogen phosphate, and acid chlorides, alkali metal salts, and ammonium salts of these.

Examples of polymerizable monomers having a pyrophosphoric acid group include bis[2-(meth)acryloyloxyethyl]pyrophosphate, bis[4-(meth)acryloyloxybutyl]pyrophosphate, bis[6-(meth)acryloyloxyhexyl]pyrophosphate, bis[8-(meth)acryloyloxyoctyl]pyrophosphate, bis[10-(meth)acryloyloxydecyl]pyrophosphate, and acid chlorides, alkali metal salts, and ammonium salts of these.

Examples of polymerizable monomers having a thiophosphoric acid group include 2-(meth)acryloyloxyethyl dihydrogen thiophosphate, 3-(meth)acryloyloxypropyl dihydrogen thiophosphate, 4-(meth)acryloyloxybutyl dihydrogen thiophosphate, 5-(meth)acryloyloxypentyl dihydrogen thiophosphate, 6-(meth)acryloyloxyhexyl dihydrogen thiophosphate, 7-(meth)acryloyloxyheptyl dihydrogen thiophosphate, 8-(meth)acryloyloxyoctyl dihydrogen thiophosphate, 9-(meth)acryloyloxynonyl dihydrogen thiophosphate, 10-(meth)acryloyloxydecyl dihydrogen thiophosphate, 11-(meth)acryloyloxyundecyl dihydrogen thiophosphate, 12-(meth)acryloyloxydodecyl dihydrogen thiophosphate, 16-(meth)acryloyloxyhexadecyl dihydrogen thiophosphate, 20-(meth)acryloyloxyeicosyl dihydrogen thiophosphate, and acid chlorides, alkali metal salts, and ammonium salts of these.

Examples of polymerizable monomers having a phosphonic acid group include 2-(meth)acryloyloxyethylphenyl phosphonate, 5-(meth)acryloyloxypentyl-3-phosphonopropionate, 6-(meth)acryloyloxyhexyl-3-phosphonopropionate, 10-(meth)acryloyloxydecyl-3-phosphonopropionate, 6-(meth)acryloyloxyhexyl-3-phosphonoacetate, 10-(meth)acryloyloxydecyl-3-phosphonoacetate, and acid chlorides, alkali metal salts, and ammonium salts of these.

Examples of polymerizable monomers having a sulfonic acid group include 2-(meth)acrylamide-2-methylpropanesulfonic acid, styrenesulfonic acid, and 2-sulfoethyl (meth)acrylate.

Examples of polymerizable monomers having a carboxylic acid group include polymerizable monomers having one carboxyl group within the molecule, and polymerizable monomers having more than one carboxyl group within the molecule.

Examples of polymerizable monomers having one carboxyl group within the molecule include (meth)acrylic acid, N-(meth)acryloylglycine, N-(meth)acryloylaspartic acid, O-(meth)acryloyltyrosine, N-(meth)acryloyltyrosine, N-(meth)acryloylphenylalanine, N-(meth)acryloyl-p-aminobenzoic acid, N-(meth)acryloyl-o-aminobenzoic acid, p-vinyl benzoic acid, 2-(meth)acryloyloxybenzoic acid, 3-(meth)acryloyloxybenzoic acid, 4-(meth)acryloyloxybenzoic acid, N-(meth)acryloyl-5-aminosalicylic acid, N-(meth)acryloyl-4-aminosalicylic acid, 2-(meth)acryloyloxyethyl hydrogen succinate, 2-(meth)acryloyloxyethyl hydrogen phthalate, 2-(meth)acryloyloxyethyl hydrogen malate, and acid halides of these.

Examples of polymerizable monomers having more than one carboxyl group within the molecule include 6-(meth)acryloyloxyhexane-1,1-dicarboxylic acid, 9-(meth)acryloyloxynonane-1,1-dicarboxylic acid, 10-(meth)acryloyloxydecane-1,1-dicarboxylic acid, 11-(meth)acryloyloxyundecane-1,1-dicarboxylic acid, 12-(meth)acryloyloxydodecane-1,1-dicarboxylic acid, 13-(meth)acryloyloxytridecane-1,1-dicarboxylic acid, 4-(meth)acryloyloxyethyl trimellitate, 4-(meth)acryloyloxyethyl trimellitate anhydride, 4-(meth)acryloyloxybutyl trimellitate, 4-(meth)acryloyloxyhexyl trimellitate, 4-(meth)acryloyloxydecyl trimellitate, 2-(meth)acryloyloxyethyl-3'-(meth)acryloyloxy-2'-(3,4-dicarboxybenzoyloxy)propyl succinate, and acid anhydrides or acid halides of these.

The polymerizable monomer having an acidic group may be used alone, or two or more thereof may be used in combination. In view of high bond strength to dental adherends, the polymerizable monomer having an acidic group is preferably one or more selected from the group consisting of a polymerizable monomer having a phosphoric acid group, a polymerizable monomer having a carboxylic acid group, and a polymerizable monomer having a sulfonic acid group, more preferably one or more selected from the group consisting of a polymerizable monomer having a phosphoric acid group with two or more hydroxyl groups bound to the phosphorus atom, a polymerizable monomer having a plurality of carboxyl groups within the molecule, and a polymerizable monomer having a sulfonic acid group, even more preferably one or more selected from the group consisting of 10-(meth)acryloyloxydecyl dihydrogen phosphate, 1,3-di (meth)acryloyloxypropyl dihydrogen phosphate, 2-(meth) acryloyloxyethyl dihydrogen phosphate, 4-(meth)acryloyloxyethyl trimellitate anhydride, 4-(meth)acryloyloxyethyl trimellitate, 2-(meth)acrylamide-2-methylpropanesulfonic acid, and 11-(meth)acryloyloxyundecane-1,1-dicarboxylic acid.

The polymerizable monomer having no acidic group is a polymerizable monomer that does not have an acidic group, and that polymerizes through a polymerization reaction initiated by a polymerization initiator. Preferred examples of the polymerizable monomer having no acidic group include water-soluble polymerizable monomers, and hydrophobic polymerizable monomers. In the present invention, the polymerizable monomer having no acidic group may be used alone, or two or more thereof may be used in combination.

Here, "water-soluble polymerizable monomer" means a polymerizable monomer having at least 10 mass % solubility in water at 25° C. The water-soluble polymerizable monomer is preferably one having at least 30 mass % solubility in water at 25° C., more preferably one that can dissolve in water at 25° C. in any proportions. The water-soluble polymerizable monomer promotes penetration of components into tooth structure. The water-soluble polymerizable monomer itself also penetrates into tooth structure, and adheres to the organic component (collagen) in the tooth structure. The water-soluble polymerizable monomer has at least one hydrophilic group such as a hydroxyl group, an oxymethylene group, an oxyethylene group, an oxypropylene group, and an amide group. Examples of the water-soluble polymerizable monomer include hydrophilic monofunctional (meth)acrylate polymerizable monomers such as 2-hydroxyethyl (meth)acrylate, 2-hydroxypropyl (meth) acrylate, 3-hydroxypropyl (meth)acrylate, 1,3-dihydroxypropyl (meth)acrylate, 2,3-dihydroxypropyl (meth)acrylate, and 2-((meth)acryloyloxy)ethyltrimethylammonium chloride; and hydrophilic monofunctional (meth)acrylamide polymerizable monomers such as N-methylol(meth)acrylamide, N-hydroxyethyl(meth)acrylamide, N,N-bis(2-hydroxyethyl)(meth)acrylamide, N-methoxymethyl(meth) acrylamide, N-ethoxymethyl(meth)acrylamide, diacetone (meth)acrylamide, N-trihydroxymethyl-N-methyl(meth) acrylamide, and N,N-diethylacrylamide. Other examples include 4-(meth)acryloylmorpholine, polyethylene glycol di(meth)acrylate (with 9 or more oxyethylene groups), and N,N',N",N'"-tetraacryloyltriethylenetetramine.

Here, "hydrophobic polymerizable monomer" means a polymerizable monomer having less than 10 mass % solubility in water at 25° C. Examples of the hydrophobic polymerizable monomer include monofunctional polymerizable monomers, aromatic bifunctional polymerizable monomers, aliphatic bifunctional polymerizable monomers, and tri- and higher-functional polymerizable monomers. The hydrophobic polymerizable monomer improves mechanical strength, ease of handling, and other properties of the paste-like composition for dental use.

Examples of the monofunctional polymerizable monomers include methyl (meth)acrylate, ethyl (meth)acrylate, propyl (meth)acrylate, isopropyl (meth)acrylate, butyl (meth)acrylate, isobutyl (meth)acrylate, benzyl (meth)acrylate, lauryl (meth)acrylate, 2-(N,N-dimethylamino)ethyl (meth)acrylate, 2,3-dibromopropyl (meth)acrylate, propylene glycol mono(meth)acrylate, glycerin mono(meth)acrylate, erythritol mono(meth)acrylate, and N-methylol(meth) acrylamide.

Examples of the aromatic bifunctional polymerizable monomers include 2,2-bis((meth)acryloyloxyphenyl)propane, 2,2-bis[4-(3-acryloyloxy-2-hydroxypropoxy)phenyl] propane, 2,2-bis[4-(3-methacryloyloxy-2-hydroxypropoxy) phenyl]propane (hereinafter, also referred to in an abbreviated form as "Bis-GMA"), 2,2-bis(4-(meth)acryloyloxyethoxyphenyl)propane, 2,2-bis(4-(meth)acryloyloxypolyethoxyphenyl)propane, 2,2-bis(4-(meth)acryloyloxydiethoxyphenyl)propane, 2,2-bis(4-(meth) acryloyloxytriethoxyphenyl)propane, 2,2-bis(4-(meth) acryloyloxytetraethoxyphenyl)propane, 2,2-bis(4-(meth) acryloyloxypentaethoxyphenyl)propane, 2,2-bis(4-(meth) acryloyloxydipropoxyphenyl)propane, 2-(4-(meth) acryloyloxydiethoxyphenyl)-2-(4-(meth) acryloyloxyethoxyphenyl)propane, 2-(4-(meth) acryloyloxydiethoxyphenyl)-2-(4-(meth) acryloyloxytriethoxyphenyl)propane, 2-(4-(meth) acryloyloxydipropoxyphenyl)-2-(4-(meth) acryloyloxytriethoxyphenyl)propane, 2,2-bis(4-(meth) acryloyloxypropoxyphenyl)propane, 2,2-bis(4-(meth) acryloyloxyisopropoxyphenyl)propane, and 1,4-bis(2-(meth)acryloyloxyethyl)pyromellitate. Preferred are 2,2-bis [4-(3-methacryloyloxy-2-hydroxypropoxy)phenyl]propane, 2,2-bis(4-methacryloyloxypolyethoxyphenyl)propane (average number of moles of ethoxy group added: 2.6; hereinafter, also referred to in an abbreviated form as "D2.6E").

Examples of the aliphatic bifunctional polymerizable monomers include glycerol di(meth)acrylate, erythritol di(meth)acrylate, sorbitol di(meth)acrylate, mannitol di(meth)acrylate, pentaerythritol di(meth)acrylate, dipentaerythritol di(meth)acrylate, ethylene glycol di(meth)acrylate, diethylene glycol di(meth)acrylate, triethylene glycol di(meth) acrylate, propylene glycol di(meth)acrylate, butylene glycol di(meth)acrylate, neopentyl glycol di(meth)acrylate, polyethylene glycol di(meth)acrylate, 1,3-butanediol di(meth) acrylate, 1,5-pentanediol di(meth)acrylate, 1,6-hexanediol di(meth)acrylate, 1,10-decanediol di(meth)acrylate, 2,2,4-trimethylhexamethylene bis(2-carbamoyloxyethyl)dimethacrylate (hereinafter, also referred to in an abbreviated form as "UDMA"), 1,2-bis(3-methacryloyloxy-2-hydroxypropoxy)ethane, and N-methacryloyloxyethylacrylamide. Preferred are glycerol di(meth)acrylate, triethylene glycol di(meth)acrylate, neopentyl glycol dimethacrylate, 2,2,4-trimethylhexamethylene bis(2-carbamoyloxyethyl)dimethacrylate, and 1,2-bis(3-methacryloyloxy-2-hydroxypropoxy)ethane.

Examples of the tri- and higher-functional polymerizable monomers include trimethylolpropane tri(meth)acrylate, trimethylolethane tri(meth)acrylate, trimethylolmethane tri (meth)acrylate, pentaerythritol tri(meth)acrylate, pentaerythritol tetra(meth)acrylate, dipentaerythritol tri(meth) acrylate, dipentaerythritol tetra(meth)acrylate, dipentaerythritol penta(meth)acrylate, N,N-(2,2,4-trimethylhexamethylene)bis[2-(aminocarboxy)propane-1,3-diol]tetramethacry late, and 1,7-diacryloyloxy-2,2,6,6-tetraacryloyloxymethyl-4-oxaheptane.

The content of polymerizable monomer (A) is preferably 5 to 60 parts by mass, more preferably 10 to 50 parts by mass, even more preferably 10 to 45 parts by mass in total 100 parts by mass of a paste-like composition for dental use of the present invention.

A paste-like composition for dental use of the present invention comprises a filler (B). The filler (B) may be any filler used in dentistry, provided that it has the average particle diameters specified by the present invention. Examples include inorganic fillers, organic fillers, and composite fillers of inorganic filler and organic filler. The filler (B) may be contained alone, or two or more thereof may be used in combination.

Examples of the inorganic fillers include silica; silica-base minerals such as kaolin, clay, isinglass, and mica; and silica-base ceramics and glasses containing, for example, $Al_2O_3$, $B_2O_3$, $TiO_2$, $ZrO_2$, BaO, $La_2O_3$, SrO, ZnO, CaO, $P_2O_5$, $Li_2O$, or $Na_2O$. Examples of the glasses include lithium borosilicate glass, borosilicate glass, bioglass, lanthanum glass, barium glass, strontium glass, soda glass, zinc glass, and fluoroaluminosilicate glass. Also preferred for use as inorganic fillers are crystal quartz, hydroxyapatite, alumina, titanium oxide, yttrium oxide, zirconia, calcium phosphate, barium sulfate, aluminum hydroxide, sodium fluoride, potassium fluoride, sodium monofluorophosphate, lithium fluoride, and ytterbium fluoride. In view of adhesion and ease of handling, a particulate silica having an average primary particle diameter of 0.001 to 10 μm is preferably used. Examples of commercially available products include Aerosil® OX 50, Aerosil® 50, Aerosil® 200, Aerosil® 380, Aerosil® R972, and Aerosil® 130 (all manufactured by Nippon Aerosil Co., Ltd. under these trade names).

Examples of the organic fillers include polymethyl methacrylate, polyethyl methacrylate, polymers of polyfunctional methacrylates, polyamides, polystyrene, polyvinyl chloride, chloroprene rubber, nitrile rubber, and styrene-butadiene rubber.

Examples of the composite fillers of inorganic filler and organic filler include fillers containing inorganic fillers dispersed in organic fillers, and inorganic-organic composite fillers containing inorganic fillers coated with various polymers.

In a paste-like composition for dental use of the present invention, the filler (B) comprises a particulate filler (B-1) having an average primary particle diameter of 0.001 to 0.2 μm (hereinafter, also referred to simply as "particulate filler (B-1)"), and a filler (B-2) having an average primary particle diameter of more than 0.2 μm and 30 μm or less (hereinafter, also referred to simply as "filler (B-2)").

In view of imparting formability to the paste, the average primary particle diameter of particulate filler (B-1) is 0.001 to 0.2 μm, preferably 0.005 to 0.15 μm, more preferably 0.01 to 0.1 μm, even more preferably 0.015 to 0.05 μm. The particulate filler (B-1) is preferably an inorganic filler. The particulate filler (B-1) may be used alone, or two or more thereof may be used in combination.

In view of the mechanical strength of a cured product of the paste, the average primary particle diameter of filler (B-2) is more than 0.2 μm and 30 μm or less, preferably 0.5 to 20 μm, more preferably 1.0 to 10 μm, even more preferably 2.0 to 5.0 μm. The filler (B-2) is preferably an inorganic filler. The filler (B-2) may be used alone, or two or more thereof may be used in combination.

The average primary particle diameter of filler (B) can be adjusted to the desired average primary particle diameter using a method such as pulverization, classification, or freeze drying.

In view of stabilizing the ease of handling of the paste over the long term while providing excellent consistency and runniness and little stringiness, the particulate filler (B-1) contained in a paste-like composition for dental use of the present invention has an average secondary particle diameter of 20 μm or less, preferably 10 μm or less, more preferably 5 μm or less, even more preferably 2 μm or less. An average secondary particle diameter of more than 20 μm leads to a hard paste, and a large change occurs in ease of handling as a result of a greater amount of polymerizable monomer (A) penetrating into the spaces between secondary particles during long storage of the paste. The average secondary particle diameter of particulate filler (B-1) may be, for example, 0.2 μm or more, though the lower limit is not particularly limited.

In the present specification, the average particle diameter of filler (B) can be determined by a laser diffraction scattering method or electron microscopy of particles. Specifically, a laser diffraction scattering method is more convenient for particle size measurement of particles of 0.1 μm or more, whereas electron microscopy is a more convenient method of particle size measurement for fine particles of less than 0.1 μm. Here, 0.1 μm is a measured value by a laser diffraction scattering method.

As a specific example of a laser diffraction scattering method, the particle size may be measured by volume using, for example, a laser diffraction particle size distribution analyzer (SALD-2300, manufactured by Shimadzu Corporation) with a 0.2% sodium hexametaphosphate aqueous solution used as dispersion medium.

As a specific example of electron microscopy, filler particles may be photographed with a scanning electron microscope (SU 3800, manufactured by Hitachi High-Technologies), and the size of particles (at least 200 particles) observed in a unit field of the micrograph may be measured with image-analyzing particle-size-distribution measurement software (Mac-View, manufactured by Mountech Co., Ltd.). Here, the particle diameter is determined as an arithmetic mean value of the maximum and minimum lengths of particles, and the average particle diameter is calculated from the number of particles and the particle diameter.

In order to improve curability, mechanical strength, and ease of handling, the filler (B) may be used after a surface treatment with a known surface treatment agent such as a silane coupling agent. Examples of the surface treatment agent include vinyltrimethoxysilane, vinyltriethoxysilane, vinyltrichlorosilane, vinyltri(β-methoxyethoxy)silane, γ-methacryloyloxypropyltrimethoxysilane, γ-glycidoxypropyltrimethoxysilane, γ-mercaptopropyltrimethoxysilane, and γ-aminopropyltriethoxysilane.

In order to improve properties such as ease of handling, X-ray opacity, and mechanical strength, the content of the filler (B) in a paste-like composition for dental use of the present invention is preferably 10 to 90 parts by mass in total 100 parts by mass of the paste-like composition for dental use. Concerning lower limits, the content of filler (B) is more preferably at least 30 parts by mass, even more preferably at least 40 parts by mass, most preferably at least 50 parts by mass in total 100 parts by mass of the paste-like composition for dental use. The upper limit is more preferably at most 85 parts by mass.

A paste-like composition for dental use of the present invention may comprise other components, for example, such as a polymerization initiator, and a polymerization accelerator. Examples of the polymerization initiator include a photopolymerization initiator, and a chemical polymerization initiator. The polymerization initiator may be used alone, or two or more thereof may be used in combination.

Examples of the photopolymerization initiator include α-diketones, ketals, thioxanthones, acylphosphine oxides, and α-aminoacetophenones.

Examples of the α-diketones include camphorquinone, benzyl, and 2,3-pentanedione.

Examples of the ketals include benzyl dimethyl ketal, and benzyl diethyl ketal.

Examples of the thioxanthones include 2-chlorothioxanthone, and 2,4-diethylthioxanthone.

Examples of the acylphosphine oxides include 2,4,6-trimethylbenzoyldiphenylphosphine oxide, bis(2,4,6-trimethylbenzoyl)phenylphosphine oxide, dibenzoylphenylphosphine oxide, bis(2,6-dimethoxybenzoyl) phenylphosphine oxide, tris(2,4-dimethylbenzoyl) phosphine oxide, tris(2-methoxybenzoyl)phosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, benzoyl-bis(2,6-dimethylphenyl)phosphine oxide, 2,4,6-trimethylbenzoylethoxyphenylphosphine oxide, and water-soluble acylphosphine oxide compounds disclosed in JP H3-57916 B.

Examples of the α-aminoacetophenones include 2-benzyl-2-dimethylamino-1-(4-morpholinophenyl)-1-butanone, 2-benzyl-2-diethylamino-1-(4-morpholinophenyl)-1-butanone, 2-benzyl-2-dimethylamino-1-(4-morpholinophenyl)-1-propanone, 2-benzyl-2-diethylamino-1-(4-morpholinophenyl)-1-propanone, 2-benzyl-2-dimethylamino-1-(4-morpholinophenyl)-1-pentanone, and 2-benzyl-2-diethylamino-1-(4-morpholinophenyl)-1-pentanone.

The photopolymerization initiator may be used alone, or two or more thereof may be used in combination. The content of the photopolymerization initiator is preferably 0.005 to 10 parts by mass, more preferably 0.01 to 5 parts by mass relative to total 100 parts by mass of the polymerizable monomer components in a paste-like composition for dental use of the present invention.

For improved photocurability, the photopolymerization initiator may be used with a polymerization accelerator such as an aldehyde, a thiol compound, or a triazine compound substituted with a trihalomethyl group. Examples of the aldehyde include terephthalaldehyde, and benzaldehyde derivatives. Examples of the benzaldehyde derivatives include dimethylaminobenzaldehyde, p-methoxybenzaldehyde, p-ethoxybenzaldehyde, and p-n-octyloxybenzaldehyde. Examples of the thiol compound include 3-mercaptopropyltrimethoxysilane, 2-mercaptobenzoxazole, decanethiol, and thiobenzoic acid. The polymerization accelerator may be used alone, or two or more thereof may be used in combination. The triazine compound substituted with a trihalomethyl group may be any known compound, as long as it is an s-triazine compound having at least one trihalomethyl group such as a trichloromethyl group or a tribromomethyl group.

Examples of the chemical polymerization initiators include organic peroxides, inorganic peroxides, and transition metal complexes. These are not particularly limited, and known organic peroxides, inorganic peroxides, and transition metal complexes may be used. The organic peroxides, inorganic peroxides, and transition metal complexes may be used alone, or two or more thereof may be used in combination.

Examples of typical organic peroxides as chemical polymerization initiators include hydroperoxides, peroxyesters, ketone peroxides, peroxyketals, dialkyl peroxides, diacyl peroxides, and peroxydicarbonates. Preferred are hydroperoxides and peroxyesters. In view of the storage stability of the paste-like composition for dental use obtained, peroxyesters are most preferred. The organic peroxides may be used alone, or two or more thereof may be used in combination.

More specific examples of hydroperoxides include cumene hydroperoxide, t-butyl hydroperoxide, t-hexyl hydroperoxide, p-menthane hydroperoxide, diisopropylbenzene hydroperoxide, and 1,1,3,3-tetramethylbutyl hydroperoxide.

The peroxyesters may be any known peroxyesters, provided that the peroxy group (—OO— group) has an acyl group at one end, and a hydrocarbon group (or a similar group) at the other end. Specific examples include α,α-bis(neodecanoylperoxy)diisopropylbenzene, cumyl peroxyneodecanoate, 1,1,3,3-tetramethylbutyl peroxyneodecanoate, 1-cyclohexyl-1-methylethyl peroxyneodecanoate, t-hexyl peroxyneodecanoate, t-butyl peroxyneodecanoate, t-hexyl peroxypivalate, t-butyl peroxypivalate, 1,1,3,3-tetramethylbutyl peroxy-2-ethylhexanoate, 2,5-dimethyl-2,5-bis(2-ethylhexanoylperoxy)hexane, 1-cyclohexyl-1-methylethyl peroxy-2-ethylhexanoate, t-hexyl peroxy-2-ethylhexanoate, t-butyl peroxy-2-ethylhexanoate, t-butyl peroxyisobutyrate, t-hexyl peroxyisopropyl monocarbonate, t-butyl peroxymaleic acid, t-butyl peroxy-3,5,5-trimethylhexanoate, t-butyl peroxylaurate, 2,5-dimethyl-2,5-bis(m-toluoylperoxy)hexane, t-butyl peroxyisopropyl monocarbonate, t-butyl peroxy-2-ethylhexyl monocarbonate, t-hexyl peroxybenzoate, 2,5-dimethyl-2,5-bis(benzoylperoxy) hexane, t-butyl peroxyacetate, t-butyl peroxy-m-toluoylbenzoate, t-butyl peroxybenzoate, and bis(t-butylperoxy)isophthalate. These may be used alone, or two or more thereof may be used in combination. In view of storage stability and reactivity, t-butyl peroxymaleic acid, t-butyl peroxy-3,5,5-trimethylhexanoate, t-butyl peroxybenzoate, t-butyl peroxyisopropyl monocarbonate, t-butyl peroxy-2-ethylhexyl monocarbonate, and t-butyl peroxyacetate are preferred, and t-butyl peroxybenzoate is more preferred.

Examples of the ketone peroxides include methyl ethyl ketone peroxide, cyclohexanone peroxide, methyl cyclohexanone peroxide, methyl acetoacetate peroxide, and acetyl acetone peroxide.

Examples of the peroxyketals include 1,1-bis(t-hexylperoxy)3,3,5-trimethylcyclohexane, 1,1-bis(t-hexylperoxy)cyclohexane, 1,1-bis(t-butylperoxy)3,3,5-trimethylcyclohexanone, 1,1-bis(t-butylperoxy)cyclohexane, 1,1-bis(t-butylperoxy)cyclodecane, 2,2-bis(t-butylperoxy)butane, n-butyl 4,4-bis(t-butylperoxy)valerate, and 2,2-bis(4,4-di-t-butylperoxycyclohexyl)propane.

Examples of the dialkyl peroxides include α,α-bis(t-butylperoxy)diisopropylbenzene, dicumyl peroxide, 2,5-dimethyl-2,5-bis(t-butylperoxy)hexane, t-butylcumyl peroxide, di-t-butyl peroxide, and 2,5-dimethyl-2,5-bis(t-butylperoxy)3-hexyne.

Examples of the diacyl peroxides include isobutyryl peroxide, 2,4-dichlorobenzoyl peroxide, 3,5,5-trimethylhexanoyl peroxide, octanoyl peroxide, lauroyl peroxide, stearyl peroxide, succinic acid peroxide, m-toluoylbenzoyl peroxide, and benzoyl peroxide.

Examples of the peroxydicarbonates include di-n-propyl peroxydicarbonate, diisopropyl peroxydicarbonate, bis(4-t-butylcyclohexyl)peroxydicarbonate, di(2-ethoxyethyl)peroxydicarbonate, di(2-ethylhexyl)peroxydicarbonate, di(2-methoxybutyl)peroxydicarbonate, and di(3-methyl-3-methoxybutyl)peroxydicarbonate.

Examples of the inorganic peroxides include peroxydisulfates and peroxydiphosphates. Preferred for curability are peroxydisulfates. Specific examples of peroxydisulfates include sodium peroxydisulfate, potassium peroxydisulfate (hereinafter, also referred to in an abbreviated form as "KPS"), aluminum peroxydisulfate, and ammonium peroxydisulfate.

In view of curability, the organic peroxides and inorganic peroxides are preferably 0.01 to 5 parts by mass, more preferably 0.05 to 2 parts by mass relative to total 100 parts by mass of the polymerizable monomer components in a paste-like composition for dental use of the present invention.

Examples of the transition metal complexes include copper compounds and vanadium compounds.

The copper compounds are preferably compounds that are soluble in the polymerizable monomer components. Specific examples of such compounds include:

copper carboxylates, such as copper acetate, copper isobutyrate, copper gluconate, copper citrate, copper phthalate, copper tartarate, copper oleate, copper octylate, copper octenoate, copper naphthenate, copper methacrylate, and copper 4-cyclohexylbutyrate;

β-diketone-copper, such as copper acetylacetonate, copper trifluoroacetylacetonate, copper hexafluoroacetylacetonate, copper 2,2,6,6-tetramethyl-3,5-heptanedionate, and copper benzoylacetone;

β-ketoester-copper, such as copper ethylacetoacetate;

copper alkoxides, such as copper methoxide, copper ethoxide, copper isopropoxide, copper 2-(2-butoxyethoxy)ethoxide, and copper 2-(2-methoxyethoxy) ethoxide;

copper dithiocarbamates, such as copper dimethyldithiocarbamate;

salts of copper and inorganic acids, such as copper nitrate; and copper chloride.

These may be used alone, or two or more thereof may be used in combination as appropriate. In view of solubility and reactivity to the polymerizable monomers, preferred are copper carboxylates, β-diketone-copper, and β-ketoester-copper, and particularly preferred are copper acetate and copper acetylacetonate.

In view of curability, the content of the copper compound is preferably 0.000005 to 1 parts by mass relative to total 100 parts by mass of the polymerizable monomer components in a paste-like composition for dental use of the present invention.

Examples of the vanadium compounds include vanadium acetylacetonate, vanadyl acetylacetonate, vanadyl stearate, vanadium naphthenate, and vanadium benzoylacetonate. Particularly preferred are vanadium acetylacetonate, and vanadyl acetylacetonate.

In view of curability, the content of the vanadium compound is preferably 0.005 to 1 parts by mass relative to total 100 parts by mass of the polymerizable monomer components in a paste-like composition for dental use of the present invention.

Examples of the polymerization accelerator include aromatic amines, aliphatic amines, aromatic sulfinates, borate compounds, reducing inorganic compounds having sulfur, thiourea derivatives, benzotriazole compounds, and benzoimidazole compounds. The polymerization accelerator may be used alone, or two or more thereof may be used in combination.

The aromatic amines may be, for example, known aromatic secondary amines, or known aromatic tertiary amines. Examples of such aromatic secondary amines or aromatic tertiary amines include N,N-bis(2-hydroxyethyl)-3,5-dimethylaniline, N, N-di(2-hydroxyethyl)-p-toluidine (hereinafter, also referred to in an abbreviated form as "DEPT"), N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis (2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, and N,N-dimethyl-3,5-di-t-butylaniline. In view of redox reactivity, N,N-di(2-hydroxyethyl)-p-toluidine is preferred.

Examples of the aliphatic amines include primary aliphatic amines such as n-butylamine, n-hexylamine, and n-octylamine; secondary aliphatic amines such as diisopropylamine, dibutylamine, and N-methylethanolamine; and tertiary aliphatic amines such as N-methyldiethanolamine, N-ethyldiethanolamine, N-n-butyldiethanolamine, N-lauryldiethanolamine, 2-(dimethylamino)ethyl (meth)acrylate, N-methyldiethanolamine di(meth)acrylate, N-ethyldiethanolamine di(meth)acrylate, triethanolamine tri(meth)acrylate, triethanolamine, trimethylamine, triethylamine, and tributylamine. In view of redox reactivity, tertiary aliphatic amines are preferred, and N-methyldiethanolamine, triethanolamine, and 2-(dimethylamino)ethyl methacrylate are particularly preferred.

The content of the aromatic amine or aliphatic amine is preferably 0.01 to 10 parts by mass, more preferably 0.02 to 5 parts by mass, even more preferably 0.05 to 2 parts by mass relative to total 100 parts by mass of the polymerizable monomer components in a paste-like composition for dental use of the present invention. When the content of the aromatic amine or aliphatic amine is less than 0.01 parts by mass, the paste-like composition for dental use obtained may have a reduced bond strength to moist bodies such as the tooth structure. When the content of the aromatic amine or aliphatic amine is more than 10 parts by mass, the shade stability of the paste-like composition for dental use obtained may decrease.

Examples of the aromatic sulfinates include lithium salts, sodium salts, potassium salts, rubidium salts, cesium salts, magnesium salts, calcium salts, strontium salts, iron salts, zinc salts, ammonium salts, tetramethylammonium salts, and tetraethylammonium salts of benzenesulfinic acid, p-toluenesulfinic acid, o-toluenesulfinic acid, ethylbenzenesulfinic acid, decylbenzenesulfinic acid, dodecylbenzenesulfinic acid, 2,4,6-trimethylbenzenesulfinic acid, 2,4,6-triisopropylbenzenesulfinic acid (hereinafter, sodium salts are also referred to in an abbreviated form as "TPBSS"), chlorobenzenesulfinic acid, and naphthalenesulfinic acid. In view of curability and storage stability of the composition, lithium salts, sodium salts, potassium salts, magnesium salts, and calcium salts of 2,4,6-trimethylbenzenesulfinic acid and 2,4,6-triisopropylbenzenesulfinic acid are preferred, and lithium salts, sodium salts, potassium salts, magnesium salts, and calcium salts of 2,4,6-triisopropylbenzenesulfinic acid are more preferred.

Preferably, the aromatic sulfinate is at least partially dispersed in the composition in powder form. With the aromatic sulfinate being dispersed in powder form, a paste-like composition for dental use of the present invention can afford even a longer time for the procedure. It is also possible to even more greatly increase polymerization curability at the bond interface and inside the resin-impregnated layer because the aromatic sulfinate dissolves in water at the surface of a moist body when the composition is applied to a moist body such as the tooth structure. When dispersed in powder form, the aromatic sulfinate is preferably one having a solubility in water at ordinary temperature (25° C.) of 1 mg/100 mL or more. An aromatic sulfinate having a solubility of less than 1 mg/100 mL does not sufficiently dissolve in water at the bond interface on moist bodies when a paste-like composition for dental use of the present invention is applied to moist bodies, and cannot easily develop the effect produced by being dispersed in powder form. The aromatic sulfinate has an average particle diameter of preferably 500 μm or less, more preferably 100 μm or less, even more preferably 50 μm or less because the aromatic sulfinate easily precipitates when the particle diameter is excessively large. The average particle diameter is preferably 0.01 μm or more because an excessively small average particle diameter overly increases the specific surface area of the powder, and may impair the ease of handling of the paste-like composition for dental use. That is, the average particle diameter of the aromatic sulfinate of when it is dispersed in powder form is preferably 0.01 to 500 μm, more preferably 0.01 to 100 μm. The average particle diameter of the aromatic sulfinate can be measured using the same method used for average particle diameter measurement of filler (B).

When dispersed in powder form, the aromatic sulfinate may have various shapes, for example, such as a spherical shape, a stylus shape, a plate shape, and an irregular shape, and the shape is not particularly limited. The aromatic sulfinate may be prepared into a fine powder using a conventionally known method such as pulverization or freeze drying.

The content of aromatic sulfinate is preferably 0.1 to 5 parts by mass, more preferably 0.2 to 4 parts by mass, even more preferably 0.5 to 3 parts by mass relative to total 100 parts by mass of the polymerizable monomer components in a paste-like composition for dental use of the present invention. When the content is less than 0.1 parts by mass or more than 5 parts by mass, the mechanical strength of a cured product of the paste-like composition for dental use may decrease.

The borate compounds are preferably arylborate compounds. Examples of the arylborate compounds include borate compounds having 1 to 4 aryl groups per molecule.

Examples of borate compounds having one aryl group per molecule include trialkyl phenylboron, trialkyl (p-chlorophenyl)boron, trialkyl (p-fluorophenyl)boron, trialkyl[3,5-bis(trifluoromethyl)phenyl]boron, trialkyl[3,5-bis(1,1,1,3,3,3-hexafluoro-2-methoxy-2-propyl)phenyl]boron, trialkyl (p-nitrophenyl)boron, trialkyl (m-nitrophenyl)boron, trialkyl (p-butylphenyl)boron, trialkyl (m-butylphenyl)boron, trialkyl (p-butyloxyphenyl)boron, trialkyl (m-butyloxyphenyl)boron, trialkyl (p-octyloxyphenyl)boron, trialkyl (m-octyloxyphenyl)boron (the alkyl groups in these example compounds are, for example, n-butyl, n-octyl, and n-dodecyl), and salts of these (e.g., sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts).

Examples of borate compounds having two aryl groups per molecule include dialkyl diphenylboron, dialkyl di(p-chlorophenyl)boron, dialkyl di(p-fluorophenyl)boron, dialkyl di[3,5-bis(trifluoromethyl)phenyl]boron, dialkyl di[3,5-bis(1,1,1,3,3,3-hexafluoro-2-methoxy-2-propyl)phenyl]boron, dialkyl di(p-nitrophenyl)boron, dialkyl di(m-nitrophenyl)boron, dialkyl di(p-butylphenyl)boron, dialkyl di(m-butylphenyl)boron, dialkyl di(p-butyloxyphenyl)boron, dialkyl di(m-butyloxyphenyl)boron, dialkyl di(p-octyloxyphenyl)boron, dialkyl di(m-octyloxyphenyl)boron (the alkyl groups in these example compounds are, for example, n-butyl, n-octyl, and n-dodecyl), and salts of these (e.g., sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts).

Examples of borate compounds having three aryl groups per molecule include monoalkyl triphenylboron, monoalkyl tri(p-chlorophenyl)boron, monoalkyl tri(p-fluorophenyl)boron, monoalkyl tri[3,5-bis(trifluoromethyl)phenyl]boron, monoalkyl tri[3,5-bis(1,1,1,3,3,3-hexafluoro-2-methoxy-2-propyl)phenyl]boron, monoalkyl tri(p-nitrophenyl)boron, monoalkyl tri(m-nitrophenyl)boron, monoalkyl tri(p-butylphenyl)boron, monoalkyl tri(m-butylphenyl)boron, monoalkyl tri(p-butyloxyphenyl)boron, monoalkyl tri(m-butyloxyphenyl)boron, monoalkyl tri(p-octyloxyphenyl)boron, monoalkyl tri(m-octyloxyphenyl)boron (the alkyl groups in these example compounds are, for example, n-butyl, n-octyl, and n-dodecyl group), and salts of these (e.g., sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts).

Examples of borate compounds having four aryl groups per molecule include tetraphenylboron, tetrakis(p-chlorophenyl)boron, tetrakis(p-fluorophenyl)boron, tetrakis[3,5-bis(trifluoromethyl)phenyl]boron, tetrakis[3,5-bis(1,1,1,3,3,3-hexafluoro-2-methoxy-2-propyl)phenyl]boron, tetrakis(p-nitrophenyl)boron, tetrakis(m-nitrophenyl)boron, tetrakis(p-butylphenyl)boron, tetrakis(m-butylphenyl)boron, tetrakis (p-butyloxyphenyl)boron, tetrakis(m-butyloxyphenyl) boron, tetrakis(p-octyloxyphenyl)boron, tetrakis(m-octyloxyphenyl)boron, (p-fluorophenyl)triphenylboron, [3,5-bis(trifluoromethyl)phenyl]triphenylboron, (p-nitrophenyl)triphenylboron, (m-butyloxyphenyl)triphenylboron, (p-butyloxyphenyl)triphenylboron, (m-octyloxyphenyl)triphenylboron, (p-octyloxyphenyl)triphenylboron, and salts of these (e.g., sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts).

In view of storage stability, preferred as arylborate compounds are borate compounds having three or four aryl groups per molecule. The arylborate compounds may be used alone, or two or more thereof may be used in combination.

Examples of the reducing inorganic compounds having sulfur (hereinafter, also referred to simply as "reducing inorganic compounds") include sulfites, bisulfites, pyrosulfites, thiosulfates, thionates, and dithionites. Preferred are sulfites and bisulfites. Specific examples include sodium sulfite, potassium sulfite, calcium sulfite, ammonium sulfite, sodium bisulfite, and potassium bisulfite. These may be used alone, or two or more thereof may be used in combination.

Preferably, the reducing inorganic compound having sulfur is at least partially dispersed in the composition in powder form. With the reducing inorganic compound being dispersed in powder form, a paste-like composition for dental use of the present invention can afford even a longer time for the procedure. It is also possible to even more greatly increase polymerization curability at the bond interface and inside the resin-impregnated layer because the reducing inorganic compound dissolves in water at the surface of a moist body when the composition is applied to a moist body such as the tooth structure. When dispersed in powder form, the reducing inorganic compound is preferably one having a solubility in water at ordinary temperature (25° C.) of 1 mg/100 mL or more. A reducing inorganic compound having a solubility of less than 1 mg/100 mL does not sufficiently dissolve in water at the bond interface on moist bodies when a paste-like composition for dental use of the present invention is applied to moist bodies, and cannot easily develop the effect produced by being dispersed in powder form. The reducing inorganic compound has an average particle diameter of preferably 500 μm or less, more preferably 100 μm or less, even more preferably 50 μm or less because the reducing inorganic compound easily precipitates when the particle diameter is excessively large. The average particle diameter is preferably 0.01 μm or more because an excessively small average particle diameter overly increases the specific surface area of the powder, and may impair the ease of handling of the paste-like composition for dental use. That is, the average particle diameter of the reducing inorganic compound of when it is dispersed in powder form is preferably 0.01 to 500 μm, more preferably 0.01 to 100 μm. The average particle diameter of the reducing inorganic compound having sulfur can be measured using the same method used for average particle diameter measurement of filler (B).

When dispersed in powder form, the reducing inorganic compound may have various shapes, for example, such as a spherical shape, a stylus shape, a plate shape, and an irregular shape, and the shape is not particularly limited. The reducing inorganic compound may be prepared into a fine powder using a conventionally known method such as pulverization or freeze drying.

The content of the reducing inorganic compound is preferably 0.01 to 15 parts by mass, more preferably 0.05 to 10 parts by mass, even more preferably 0.1 to 5 parts by mass relative to total 100 parts by mass of the polymerizable monomer components in a paste-like composition for dental use of the present invention. When the content is less than 0.01 parts by mass, the paste-like composition for dental use obtained may have a reduced bond strength to moist bodies such as the tooth structure. When the content is more than 15 parts by mass, the mechanical strength of a cured product of the paste-like composition for dental use obtained may decrease.

Examples of the thiourea derivatives include ethylenethiourea, 4,4-dimethylethylenethiourea, N,N'-dimethylthiourea, N,N'-diethylthiourea, N,N'-di-n-propylthiourea, dicyclohexylthiourea, trimethylthiourea, triethylthiourea, tri-n-propylthiourea, tricyclohexylthiourea, tetramethylthiourea, tetraethylthiourea, tetra n-propylthiourea, dicyclohexylthiourea, tetracyclohexylthiourea, N-acetylthiourea, N-benzoylthiourea, diphenylthiourea, and pyridylthiourea. Preferred are 4,4-dimethylethylenethiourea, pyridylthiourea, and benzoylthiourea.

Examples of the benzotriazole compounds and/or benzoimidazole compounds include compounds represented by, for example, the following general formulae [I] and [II], respectively.

[Chem. 1]

[I]

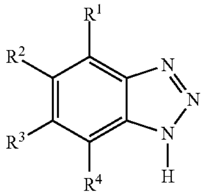

[Chem. 2]

[II]

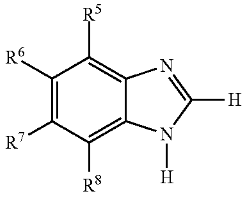

In the general formulae [I] and [II], $R^1$ to $R^8$ each independently represent a hydrogen atom, a hydroxyl group, an alkyl group, an aryl group, an alkoxy group, an alkenyl group, an aralkyl group, or a halogen atom.

The alkyl groups represented by $R^1$ to $R^8$ may be linear, branched, or cyclic, and are preferably alkyl groups having 1 to 10 carbon atoms. Specific examples include methyl, ethyl, n-propyl, isopropyl, cyclopropyl, n-butyl, isobutyl, sec-butyl, tert-butyl, cyclobutyl, n-pentyl, isopentyl, neopentyl, tert-pentyl, cyclopentyl, n-hexyl, isohexyl, cyclohexyl, n-heptyl, cycloheptanyl, n-octyl, 2-ethylhexyl, cyclooctyl, n-nonyl, cyclononyl, and n-decyl. Particularly preferred are methyl and ethyl.

The aryl groups represented by $R^1$ to $R^8$ are preferably aryl groups having 6 to 10 carbon atoms. Examples include phenyl, naphthyl, and anthryl.

The alkoxy groups represented by $R^1$ to $R^8$ may be linear, branched, or cyclic, and are preferably alkoxy groups having 1 to 8 carbon atoms. Specific examples include methoxy, ethoxy, n-propoxy, isopropoxy, n-butoxy, tert-butoxy, n-hexyloxy, cyclohexyloxy, n-octyloxy, and 2-ethylhexyloxy.

The alkenyl groups represented by $R^1$ to $R^8$ may be linear, branched, or cyclic, and are preferably alkenyl groups having 1 to 6 carbon atoms. Specific examples include vinyl, allyl, methylvinyl, propenyl, butenyl, pentenyl, hexenyl, cyclopropenyl, cyclobutenyl, cyclopentenyl, and cyclohexenyl.

Examples of the aralkyl groups represented by $R^1$ to $R^8$ include alkyl groups (particularly, alkyl groups having 1 to 10 carbon atoms) substituted with aryl groups (particularly, aryl groups having 6 to 10 carbon atoms). Specific examples include benzyl.

Examples of the halogen atoms represented by $R^1$ to $R^8$ include chlorine atoms, bromine atoms, and iodine atoms.

$R^1$ to $R^8$ are preferably hydrogen atoms or methyl groups.

The benzotriazole compounds and benzoimidazole compounds may be used alone, or two or more thereof may be used in combination. Specific examples of the benzotriazole compounds and benzoimidazole compounds include 1H-benzotriazole (hereinafter, also referred to in an abbreviated form as "BTA"), 5-methyl-1H-benzotriazole, 5,6-dimethyl-1H-benzotriazole, benzoimidazole, 5-methylbenzoimidazole, and 5,6-dimethylbenzoimidazole. In view of shades and storage stability of the composition, preferred are 1H-benzotriazole, and 5-methyl-1H-benzotriazole.

In order to impart acid resistance to tooth structure, a paste-like composition for dental use of the present invention may comprise a fluorine-ion releasing substance. Examples of the fluorine-ion releasing substance include fluorine-ion releasing polymers such as a copolymer of methyl methacrylate and methacrylic acid fluoride; fluorine-ion releasing substances such as cetylamine hydrofluoride; and inorganic fillers such as those mentioned above, including fluoroaluminosilicate glass, sodium fluoride, potassium fluoride, sodium monofluorophosphate, lithium fluoride, and ytterbium fluoride.

A paste-like composition for dental use of the present invention may comprise an additive such as a stabilizer (polymerization inhibitor), a colorant, a fluorescent agent, or a ultraviolet absorber. A paste-like composition for dental use of the present invention may also comprise an antimicrobial substance such as cetylpyridinium chloride, benzalkonium chloride, (meth)acryloyloxydodecylpyridinium bromide, (meth)acryloyloxyhexadecylpyridinium chloride, (meth)acryloyloxydecylammonium chloride, and triclosan.

A method for producing a paste-like composition for dental use of the present invention comprises the steps of:

- mixing a polymerizable monomer (A) and a particulate filler (B-1) having an average primary particle diameter of 0.001 to 0.2 μm to obtain an intermediate paste (hereinafter, also referred to as "step 1"); and
- additionally mixing the polymerizable monomer (A) with the intermediate paste to obtain a final paste as a paste-like composition for dental use (hereinafter, also referred to as "step 2"),
- the particulate filler (B-1) in the step of obtaining an intermediate paste being mixed in an amount of 30 to 150 parts by mass relative to total 100 parts by mass of the polymerizable monomer (A).

Here, "final paste" means a final-product paste-like composition for dental use. A paste-like composition for dental use of the present invention can exhibit excellent ease of handling also when the final paste obtained in the above production method is mixed with a final paste produced by a different production method that produces a final paste without producing the intermediate paste. That is, aside from showing stable consistency and runniness and little stringiness immediately after production and even after long storage, a newly produced paste-like composition for dental use of the present invention can be mixed with a paste-like composition for dental use whose paste properties have deteriorated after long storage. In this way, the paste-like composition for dental use whose paste properties have deteriorated after long storage can recover its paste properties, and the paste mixture can have excellent ease of handling.

It is important in a method of production of a paste-like composition for dental use of the present invention that the step of obtaining an intermediate paste comprises the step of mixing 30 to 150 parts by mass of particulate filler (B-1) relative to total 100 parts by mass of polymerizable monomer (A). By mixing the polymerizable monomer (A) and the particulate filler (B-1) in predetermined proportions, and kneading the mixture in this step, a hard intermediate paste can be obtained with the particulate filler (B-1) dispersed therein.

If the particulate filler (B-1) is used (added or introduced) and kneaded in step 2, the additional portion of particulate filler (B-1) does not sufficiently disperse, and may cause changes in paste properties during long storage. It is accordingly preferable that the particulate filler (B-1) used to produce the paste-like composition for dental use be introduced in full amount in step 1, and dispersed in polymerizable monomer (A) to obtain an intermediate paste. In other words, it is preferable in certain embodiments of a method of production of a paste-like composition for dental use of the present invention that no additional particulate filler (B-1) be added or mixed with the intermediate paste in step 2 because a paste-like composition for dental use produced by such a method can have more stable paste properties during long storage, and shows stable consistency and runniness and little stringiness immediately after production and even after long storage.

In step 1, it is preferable that the polymerizable monomer (A) used in the production method of a paste-like composition for dental use be not introduced in total 100 parts by mass but added in an amount of 20 to 90 parts by mass, instead of the full amount. The optimum range of the amount of polymerizable monomer introduced for the preparation of an intermediate paste depends on factors such as the viscosity of the polymerizable monomer, and the type of filler. The polymerizable monomer (A) is added in an amount of more preferably 30 to 90 parts by mass, even more preferably 35 to 85 parts by mass of total 100 parts by mass of polymerizable monomer (A). By being added in an amount of 20 parts by mass or greater, the polymerizable monomer (A) can more easily blend with the particulate filler (B-1) into a paste form. By introducing 90 parts by mass or less of polymerizable monomer (A), the intermediate paste can have a moderate viscosity that allows the particulate filler (B-1) to sufficiently disperse, and the paste properties show excellent stability during long storage. In step 1, the particulate filler (B-1) is added in an amount of 30 to 150 parts by mass, preferably 32 to 100 parts by mass, more preferably 35 to 95 parts by mass, even more preferably 37 to 90 parts by mass relative to total 100 parts by mass of polymerizable monomer (A).

A method of production of a paste-like composition for dental use of the present invention comprises the step (step 2) of additionally mixing the polymerizable monomer (A) with the intermediate paste to obtain a final paste. With step, the particulate filler (B-1) can have an average secondary particle diameter of 20 μm or less. The amount of polymerizable monomer (A) added in step 2 is not particularly limited, and may be 10 to 80 parts by mass when the total amount of polymerizable monomer (A) used in the production method of a paste-like composition for dental use is 100 parts by mass. The polymerizable monomer introduced in step 2 may be kneaded after being introduced at once, or after being introduced in divided portions. The polymerizable monomer may be kneaded after being introduced together with a filler (B-2) having an average primary particle diameter of 0.2 μm to 30 μm (described below), or may be kneaded after being separately introduced from the filler (B-2).

A method of production of a paste-like composition for dental use of the present invention may comprise the step of introducing and kneading a filler (B-2) having an average primary particle diameter of more than 0.2 μm and 30 μm or less. All or a part of the filler (B-2) may be introduced and kneaded in step 1. All or a part of the filler (B-2) may be introduced and kneaded in step 2, simultaneously with a part of the polymerizable monomer (A). Alternatively, all or a part of the filler (B-2) may be introduced and kneaded in a step different from step 2.

In a method of production of a paste-like composition for dental use of the present invention, a liquid composition containing polymerizable monomer (A) may be mixed with the filler (B) using an ordinary kneading machine. For example, it is preferable to use a biaxial kneading machine (twin mix), a triaxial kneading machine, (tri mix), or a kneader for kneading of a high-viscosity paste, and to use a planatary mixer for kneading of a low-viscosity paste.

In view of ensuring stable paste properties in the final paste, the intermediate paste produced for the production of a paste-like composition for dental use of the present invention has a consistency that is preferably 5 to 20 mm, more preferably 7 to 18 mm, even more preferably 10 to 16 mm. In this specification, "consistency" means the extent of spread of when a paste (for example, a paste of the paste-like composition for dental use, or the intermediate paste) is squashed under a certain load, and higher consistency values mean that the paste is softer, and lower consistency values mean that the paste is harder. The method of consistency measurement is as described in the EXAMPLES section below.

In view of ensuring ease of handling and stable paste properties in the paste, a paste-like composition for dental use of the present invention has a consistency of 15 to 40 mm, preferably 16 to 38 mm, more preferably 17 to 36 mm, even more preferably 18 to 34 mm. Preferably, the consistency of a paste-like composition for dental use of the present invention falls in these ranges after an elapsed time period of 2 years at 25° C. The method of consistency measurement is as described in the EXAMPLES section below.

A paste-like composition for dental use of the present invention is not limited to particular uses, and can be used as a dental material. Specifically, a paste-like composition for dental use of the present invention can be suitably used as a dental composite resin (for example, a dental filling composite resin, a composite resin for crowns, a dental composite resin for abutment construction), a denture base resin, a denture base liner, an impression material, a luting material (for example, a dental resin cement, a resin-added glass ionomer cement), a dental bonding agent (for example, an orthodontic adhesive, a bonding agent for application to cavities), or a tooth fissure sealant. A cured product of a paste-like composition for dental use of the present invention can be suitably used as, for example, a CAD/CAM resin block, a temporary crown, or an artificial teeth material. Because a paste-like composition for dental use of the present invention shows stable consistency and runniness and little stringiness immediately after production and even after long storage, a paste-like composition for dental use of the present invention is particularly suited for use as a dental composite resin, a dental resin cement, or a dental composite resin for abutment construction.

The present invention encompasses embodiments combining the foregoing features, provided that the present invention can exhibit its effects with such combinations made in various forms within the technical idea of the present invention.

EXAMPLES

The following describes the present invention in greater detail by way of Examples. It is to be noted, however, that the present invention is in no way limited by the following Examples, and various changes may be made by a person with ordinary skill in the art within the technical idea of the present invention. The abbreviations and symbols used are as follows.

Polymerizable Monomer (A)

Acidic Group-Containing Polymerizable Monomer

MDP: 10-Methacryloyloxydecyl dihydrogen phosphate

Polymerizable Monomer Having No Acidic Group

3G: Triethylene glycol dimethacrylate

Bis-GMA: 2,2-Bis[4-(3-methacryloyloxy-2-hydroxypropoxy)phenyl]propane

D2.6E: 2,2-Bis(4-methacryloyloxypolyethoxyphenyl) propane (average number of moles of ethoxy group added: 2.6)

#801: 1,2-Bis(3-methacryloyloxy-2-hydroxypropoxy) ethane

Filler (B)

Particulate Filler (B-1)

Ar 130-treated product: Aerosil® 130 (manufactured by Nippon Aerosil Co., Ltd.) was surface treated with 3-methacryloyloxypropyltrimethoxysilane to obtain an Ar 130-treated product (average primary particle diameter: 16 nm), using an ordinary method.

OX 50-treated product: Aerosil® OX 50 (manufactured by Nippon Aerosil Co., Ltd.) was surface treated with 3-methacryloyloxypropyltrimethoxysilane to obtain an OX 50-treated product (average primary particle diameter: 40 nm), using an ordinary method.

Alumina: AEROXIDE® Alu C (manufactured by Nippon Aerosil Co., Ltd.; average primary particle diameter: 20 nm) was used without any modification.

Filler (B-2)

F1: Barium glass (E-3000 Barium Silicate Glass, manufactured by Esstech with the product code V-117-1190) was pulverized with a ball mill, and treated with hydrochloric acid to obtain a barium glass powder. The barium glass powder (100 parts by mass) was surface treated with 3 parts by mass of 3-methacryloyloxypropyltrimethoxysilane to obtain F1 (average primary particle diameter: 2.5 μm), using an ordinary method.

F2: Barium glass (product code 8235 K4, manufactured by Schott) was pulverized with a ball mill, and treated with hydrochloric acid to obtain a barium glass powder. The barium glass powder (100 parts by mass) was surface treated with 3 parts by mass of 3-methacryloyloxypropyltrimethoxysilane to obtain F2 (average primary particle diameter: 2.3 μm), using an ordinary method.

F3: Barium glass (Raysorb E-3000, manufactured by Esstech under this trade name) was pulverized with a ball mill to obtain a barium glass powder. The barium glass powder (100 parts by mass) was surface treated with 3 parts by mass of 3-methacryloyloxypropyltrimethoxysilane to obtain F3 (average primary particle diameter: 2.5 μm), using an ordinary method.

Photopolymerization Initiator

CQ: Camphorquinone

Chemical Polymerization Initiator

CuA: Copper(II) acetate

BPO: Benzoyl peroxide

BPB: t-Butyl peroxybenzoate

KPS: Potassium peroxydisulfate

THP: 1,1,3,3-Tetramethylbutyl hydroperoxide

Polymerization Accelerator

TPBSS: Sodium 2,4,6-triisopropylbenzenesulfinate

DEPT: N,N-Bis(2-hydroxyethyl)-p-toluidine

BTA: 1H-Benzotriazole $Na_2SO_3$: Sodium sulfite

DMETU: 4,4-Dimethylethylenethiourea

Other

PDE: Ethyl 4-(N,N-dimethylamino)benzoate (polymerization accelerator for photopolymerization initiator)

BHT: 2,6-Di-t-butyl-4-methylphenol (stabilizer)

Average Primary Particle Diameter of Filler (B)

The average primary particle diameter of filler (B) was measured as follows. For fillers with an average primary particle diameter of 0.10 μm or more, the average primary particle diameter was measured by volume using a laser diffraction particle size distribution analyzer (SALD-2300, manufactured by Shimadzu Corporation). A 0.2% sodium hexametaphosphate aqueous solution was used as dispersion medium. For fillers (particulate filler (B-1)) with an average primary particle diameter of less than 0.10 μm, the average primary particle diameter was measured by, for example, taking a photograph of particles with a field-emission transmission electron microscope (HF-3300, manufactured by Hitachi High-Technologies), and measuring the size of particles (at least 200 particles) observed in a unit field of the micrograph, using image-analyzing particle-size-distribution measurement software (Mac-View, manufactured by Mountech Co., Ltd.) (n=1). Here, the particle diameter is determined as an arithmetic mean value of the maximum and minimum lengths of particles, and the average primary particle diameter is calculated from the number of particles and the particle diameter.

Average Secondary Particle Diameter of Filler (B)

The average secondary particle diameter of filler (B) was measured as follows. A cured product of an intermediate paste or a final paste was prepared, and particles in a cross section of the cured product were photographed with a scanning electron microscope (SU3800, manufactured by Hitachi High-Technologies). The size of secondary particles (at least 200 particles) observed in a unit field of the micrograph was then measured with image-analyzing particle-size-distribution measurement software (Mac-View, manufactured by Mountech Co., Ltd.) (n=1). Here, the diameter of a secondary particle is determined as the diameter of a corresponding circle having the same area as the secondary particle, and the average particle diameter is calculated from the number of secondary particles and the particle diameter.

Examples 1 to 20 and Comparative Examples 1 to 8

Production of Paste-Like Composition for Dental Use

For each Example and Comparative Example shown in Tables 1 and 2, the polymerizable monomer (A) was stirred with all the other components except for the filler (B), using a mechanical stirrer. The mixture was stirred until a homogenous solution containing no observable insoluble matter was obtained. This produced a polymerizable monomer-containing composition.

The polymerizable monomer-containing composition was then kneaded with the filler (B) in the proportions presented in Tables 1 and 2 for each Example and Comparative Example. These were kneaded with a twin mixer (all-purpose mixing stirrer STX-03, manufactured by Dalton Corporation) until the whole mixture turned homogenous. This produced an intermediate paste. After degassing, the intermediate paste was measured for consistency according to the method described below. The intermediate paste was then kneaded with the polymerizable monomer-containing composition and the filler (B) using a twin mixer (all-purpose mixing stirrer STX-03, manufactured by Dalton Corporation) in the proportions presented for each Example and Comparative Example. These were kneaded until the whole mixture turned homogenous. This produced a final paste. The paste was determined as being homogenous when there were no observable aggregated clumps of filler after a portion of the paste was sandwiched between two glass plates. In Comparative Examples 4, 5, and 6, the final paste was obtained by kneading the polymerizable monomer-containing composition with the whole filler (B), without preparing the intermediate paste.

The properties of the final pastes produced as above were evaluated according to the methods described below. In Examples 1 to 13 and Comparative Examples 1 to 6, the final paste in Tables 1 and 2 was filled into a polyolefinic resin syringe immediately after production, and was evaluated as a paste-like composition for dental use immediately after being filled into the syringe (hereinafter, "immediately after production"), and after being left to stand in a 25° C. constant-temperature environment for 2 years. In Examples 14 to 20 and Comparative Examples 7 and 8, the final pastes of the first and second agents shown in Table 3 were filled into a 5 ml double syringe (manufactured by SULZER MIXPAC) immediately after production. Immediately after being filled into the syringe (hereinafter, "immediately after production"), and after being left to stand in a 25° C. constant-temperature environment for 2 years, the two agents were automatically mixed at a 1:1 volume ratio by pushing the paste out of the double syringe with a plunger set on the syringe and with a mixing tip (equipped with a 0.9 mm guide tip, manufactured by SULZER MIXPAC) attached to the tip of the double syringe. The mixture was then evaluated as a paste-like composition for dental use. The results are presented in Tables 1 to 3. In Tables 1 and 2, "(A)+other" means the amount of a mixture of the polymerizable monomer (A) and all the other components except for the filler (B). A paste prepared as a two-paste composition by mixing the paste of Comparative Example 5 (second agent) and the final paste of Example 6 (first agent) also had excellent properties because of the final paste of Example 6 contained in the paste, as demonstrated in Example 19.

Test Methods

Consistency

A plastic board was placed over a measured 0.5 cc portion of the intermediate paste or final paste (paste-like composition for dental use) of each Example and Comparative Example, and a 40 g load, including the mass of the plastic board, was applied through the plastic board for 120 seconds to crush the paste. The resulting paste, spread in a circular disc shape, was then measured for maximum diameter and minimum diameter, and the average (mm) of these diameters was determined as the consistency (n=3). A mean value of these consistency values was then calculated.

Runniness

Runniness as an index of paste flowability was evaluated as follows. A needle tip with a 20 G (gauge) needle was attached to a syringe filled with the final paste of Example and Comparative Example shown in Tables 1 and 2. Separately, the mixing tip (equipped with a 0.9 mm guide tip) was attached to a double syringe filled with the final paste of Example and Comparative Example shown in Table 3. In a 37° C. environment, 30 mg of each paste was extruded to dental mixing paper, and the distance (mm) traveled by the paste in 1 minute after the mixing paper was turned vertical was measured (n=5). From the measured values, a mean value was calculated as the runniness of the paste-like composition for dental use. The preferred difference between the runniness immediately after production and the runniness after 2 years at 25° C. is 2.5 mm or less, more preferably 2.3 mm or less, even more preferably 2.2 mm or less.

Stringiness

A needle tip with a 20 G needle was attached to a syringe filled with the final paste of Example and Comparative Example shown in Tables 1 and 2. Separately, the mixing tip was attached to a double syringe filled with the final paste of Example and Comparative Example shown in Table 3. The paste (30 mg) was extruded to dental mixing paper, and the presence or absence of stringiness of when the end of the needle or mixing tip was moved away from the paste was visually confirmed (n=5). Here, the end of the needle or mixing tip was moved away at a rate of 5 cm/s. The results were evaluated using the following criteria.

Good: None of the samples had stringiness.

Acceptable: One or more samples had stringiness and the string broke after the needle or mixing tip was moved 5 cm.

Poor: One or more samples had stringiness that persisted beyond 5 cm.

Discharge Force

The mixing tip (equipped with a 0.9 mm guide tip) was attached to a double syringe filled with the final paste of Example and Comparative Example shown in Table 3. With the syringe container vertically set, a universal testing machine (Autograph AG-I, 100 kN, manufactured by Shimadzu Corporation under this trade name) was used to eject the paste through the syringe aperture with a piston attached to the syringe, under the load applied by lowering the crosshead at a rate of 4 mm/min after attaching a jig for compression strength testing to the crosshead. The maximum load was determined as the discharge force (n=5), and a mean value of the measured values was calculated. The discharge force measurement was conducted at 25° C. A discharge force of 40 N or less means that the paste is easily ejectable, and has good ejectability. A discharge force of 40 N to 60 N means that the paste is ejectable but the ejectability is inferior. A discharge force of 60 N or more means that the paste is not easily ejectable, and the ejectability is poor.

Flexural Strength

The final paste of Example and Comparative Example shown in Table 3 was filled into a stainless-steel mold (dimensions: 2 mm×2 mm×25 mm). With the paste being pressed between glass slides from top and bottom, light was applied through the glass slides from both sides to cure the paste and obtain a cured product specimen. Here, light was applied at 5 points each side, 10 seconds at each point, using a dental LED photoirradiator for polymerization (PenCure 2000 manufactured by J. Morita Corp. under this trade name). A total of 5 cured products were prepared for each Example and Comparative Example. The cured product was stored in 37° C. distilled water for 24 hours after being taken out of the mold. In order to measure flexural strength and flexural modulus, the specimens were tested in a three-point flexural test conducted according to JIS T 6514:2015 and ISO 4049:2009 at a span length of 20 mm and a crosshead speed of 1 mm/min, using a universal testing machine (Autograph AG-I, 100 kN, manufactured by Shimadzu Corporation under this trade name) (n=5). From the measured values, a mean value was calculated for each specimen to find the flexural strength and flexural modulus.

Marginal Sealing

A cavity measuring approximately 2 mm in diameter and approximately 1 mm in depth was created in a portion of an extracted human molar centering on the cervical line, using a dental air turbine. The cavity was filled with the final paste of Example and Comparative Example shown in Table 3, and the paste was cured by applying light for 20 seconds with a dental LED photoirradiator for polymerization (PenCure 2000 manufactured by J. Morita Corp. under this trade name). In order to prevent penetration of a dye through the root apex, crown fissures, and other parts of the tooth, a bonding agent of a commercially available dental adhesive (Clearfil® Mega Bond®, manufactured by Kuraray Noritake Dental Inc. under this trade name) was applied to the tooth, excluding the cavity restored portion and its peripheral area. The bonding agent was cured by applying light for 30 seconds with the photoirradiator. The specimen was subjected to a load of thermal cycling by being immersed first in a 0.2% basic aqueous solution of fuchsine (an aqueous solution containing a dye) at 25° C. for 24 hours, and then in 4° C. cold water and in 60° C. hot water, one minute each. After repeating this thermal cycle 3,000 times, the specimen was immersed again in a 0.2% basic aqueous solution of fuchsine for 10 minutes, and washed with water after being taken out of the solution. The specimen was vertically divided into three portions in the area filled with the paste to prepare three sections per tooth, using a low-speed diamond cutter. A total of 9 sections were prepared from three human molars. The specimen was determined as "Good" when none of the 9 sections had dye penetration, and "Poor" when penetration of dye was observed in one or more sections.

TABLE 1

| | | | | Ex. 1 | Ex. 2 | Ex. 3 | Ex. 4 | Ex. 5 | Ex. 6 |
|---|---|---|---|---|---|---|---|---|---|
| Composition of paste-like composition for dental use (parts by mass) | Polymerizable monomer (A) | Polymerizable monomer having acidic group | MDP | 20 | 20 | 20 | 20 | 20 | |
| | | Polymerizable monomer having no acidic group | Bis-GMA | 25 | 25 | 25 | 35 | 35 | 35 |
| | | | D2.6E | 40 | 40 | 40 | 30 | 30 | 25 |
| | | | 3G | 15 | 15 | 15 | 15 | 15 | 40 |
| | Other | Chemical polymerization initiator | CuA | 0.0004 | | | 0.00025 | 0.00025 | |
| | | | BPO | | 3 | 3 | | | 1.5 |
| | | | BPB | 0.5 | | | 0.5 | 0.5 | |
| | | | KPS | 3 | | | 1 | 1 | |
| | | | THP | | | | | | |
| | | Photopolymerization initiator | CQ | 0.15 | 0.15 | 0.15 | 0.15 | 0.15 | 1 |
| | | Other | BHT | 0.2 | 0.2 | 0.2 | 0.15 | 0.15 | 0.05 |
| | Filler (B) | B-1 | Ar 130-treated product | 30 | | | 30 | 30 | |
| | | | OX 50-treated product | | 30 | 30 | | | 30 |
| | | B-2 | F1 | 200 | 200 | 200 | 200 | 200 | |
| | | | F2 | | | | | | 200 |

TABLE 1-continued

| | | | | | | | | | |
|---|---|---|---|---|---|---|---|---|---|
| Production process of paste-like composition for dental use | Intermediate paste | Composition (parts by mass) | (A) + other | 40 | 70 | 75 | 50 | 50 | 80 |
| | | | B-1 | 30 | 30 | 30 | 30 | 30 | 30 |
| | | | B-2 | 0 | 200 | 200 | 0 | 200 | 200 |
| | | Average particle diameter of filler (μm) | B-1 (Average primary particle diameter) | 0.016 | 0.04 | 0.04 | 0.016 | 0.016 | 0.04 |
| | | | B-1 (Average secondary particle diameter) | 30 | 40 | 40 | 30 | 30 | 5 |
| | | Consistency (mm) | Immediately after production | 16.5 | 17 | 17 | 15 | 13 | 13 |
| | Final paste | Composition added to intermediate paste (parts by mass) | (A) + other | 60.35 | 30.35 | 25.35 | 50.3 | 50.3 | 21.05 |
| | | | B-1 | 0 | 0 | 0 | 0 | 0 | 0 |
| | | | B-2 | 200 | 0 | 0 | 200 | 0 | 0 |
| | | Average particle diameter of filler (μm) | B-1 (Average primary particle diameter) | 0.016 | 0.04 | 0.04 | 0.016 | 0.016 | 0.04 |
| | | | B-1 (Average secondary particle diameter) | 3 | 1 | 1 | 4 | 4 | 0.5 |
| | | | B-2 (Average primary particle diameter) | 2.5 | 2.5 | 2.5 | 2.5 | 2.5 | 2.3 |
| | | | B-2 (Average secondary particle diameter) | 10 | 18 | 19 | 17 | 15 | 17 |
| Evaluation results | | Consistency (mm) | Immediately after production | 26 | 26 | 27 | 23 | 28 | 29 |
| | | | Two years at 25° C. | 24 | 27 | 27 | 24 | 30 | 28 |
| | | Runniness (mm) | Immediately after production | 0 | 0 | 0 | 0 | 0 | 0 |
| | | | Two years at 25° C. | 0 | 0 | 0 | 0 | 0 | 0 |
| | | Stringiness | Immediately after production | Good | Good | Good | Good | Good | Good |
| | | | Two years at 25° C. | Good | Good | Good | Good | Good | Good |

| | | | | Ex. 7 | Com. Ex. 1 | Com. Ex. 2 | Com. Ex. 3 | Com. Ex. 4 |
|---|---|---|---|---|---|---|---|---|
| Composition of paste-like composition for dental use (parts by mass) | Polymerizable monomer (A) | Polymerizable monomer having acidic group | MDP | 20 | 20 | 20 | 20 | 20 |
| | | Polymerizable monomer having no acidic group | Bis-GMA | 25 | 25 | 25 | 25 | 25 |
| | | | D2.6E | 40 | 40 | 40 | 40 | 40 |
| | | | 3G | 15 | 15 | 15 | 15 | 15 |
| | Other | Chemical polymerization initiator | CuA | | | | | |
| | | | BPO | | | | | |
| | | | BPB | | | | | |
| | | | KPS | | 3 | 3 | 3 | 3 |
| | | | THP | 3 | | | | |
| | | Photopolymerization initiator | CQ | 0.15 | 0.15 | 0.15 | 0.15 | 0.15 |
| | | Other | BHT | 0.2 | 0.2 | 0.2 | 0.2 | 0.2 |
| | Filler (B) | B-1 | Ar 130-treated product | 30 | 30 | 30 | 30 | 30 |
| | | | OX 50-treated product | | | | | |
| | | B-2 | F1 | 200 | 200 | 200 | 200 | 200 |
| | | | F2 | | | | | |
| Production process of paste-like composition for dental use | Intermediate paste | Composition (parts by mass) | (A) + other | 40 | 40 | 40 | 103.35 | |
| | | | B-1 | 30 | 10.5 | 4.5 | 30 | |
| | | | B-2 | 0 | 0 | 0 | 0 | |
| | | Average particle diameter of filler (μm) | B-1 (Average primary particle diameter) | 0.016 | 0.016 | 0.016 | | |
| | | | B-1 (Average secondary particle diameter) | 30 | 40 | 60 | | |
| | | Consistency (mm) | Immediately after production | 16.6 | 17 | 25 | 30 | |
| | Final paste | Composition added to intermediate paste (parts by mass) | (A) + other | 63.36 | 60.35 | 60.35 | −3 | 100.35 |
| | | | B-1 | 0 | 19.5 | 25.5 | 0 | 30 |
| | | | B-2 | 200 | 200 | 200 | 200 | 200 |
| | | Average particle diameter of filler (μm) | B-1 (Average primary particle diameter) | 0.016 | 0.016 | 0.016 | 0.016 | 0.016 |
| | | | B-1 (Average secondary particle diameter) | 3 | 25 | 100 | 100 | 100 |
| | | | B-2 (Average primary particle diameter) | 2.5 | 2.5 | 2.5 | 2.5 | 2.5 |
| | | | B-2 (Average secondary particle diameter) | 10 | 10 | 10 | 10 | 10 |
| Evaluation results | | Consistency (mm) | Immediately after production | 27 | 27 | 26 | 26 | 20 |
| | | | Two years at 25° C. | 26 | 42 | 47 | 48 | 49 |
| | | Runniness (mm) | Immediately after production | 0 | 0 | 1 | 1 | 1 |
| | | | Two years at 25° C. | 0 | 3 | 5 | 8 | 10 |

TABLE 1-continued

| | | | | | | | |
|---|---|---|---|---|---|---|---|
| Stringiness | Immediately after production | Good | Good | Accept-able | Accept-able | Accept-able |
| | Two years at 25° C. | Good | Accept-able | Poor | Poor | Poor |

TABLE 2

| | | | | Ex. 8 | Ex. 9 | Ex. 10 | Ex. 11 | Ex. 12 | Ex. 13 | Com. Ex. 5 | Com. Ex. 6 |
|---|---|---|---|---|---|---|---|---|---|---|---|
| Composition of paste-like composition for denial use (parts by mass) | Polymerizable monomer (A) | Polymerizable monomer having no acidic group | D2.6E | 80 | 80 | 80 | 80 | 80 | 80 | 75 | 80 |
| | | | 3G | 20 | 20 | 20 | 20 | 20 | 20 | 25 | 20 |
| | | | #801 | | | | | | | | |
| | Other | Polymerization accelerator | TPBSS | 3 | 3 | 3 | 3 | 3 | | | 3 |
| | | | DEPT | 0.5 | 0.5 | 0.5 | 1 | 1 | | 2.5 | 0.5 |
| | | | BTA | 3 | | | 3 | 3 | | | |
| | | | $Na_2SO_3$ | 3 | 3 | 3 | 3 | 3 | | 3 | 3 |
| | | | DMETU | | | | | | 3 | | |
| | | Other | PDE | 0.05 | 0.05 | 0.05 | 0.05 | 0.05 | 0.05 | 0.05 | 0.05 |
| | | | BHT | 0.05 | 0.05 | 0.05 | 0.05 | 0.05 | 0.05 | 0.05 | 0.05 |
| | Filler (B) | B-1 | OX 50-treated product | | 30 | 30 | | | | 5 | |
| | | | Alumina | 30 | | | 30 | 30 | 30 | 20 | 30 |
| | | B-2 | F3 | 150 | 150 | 150 | 150 | 150 | 150 | 210 | 150 |
| Production process of paste-like composition for dental use | Intermediate paste | Composition (parts by mass) | (A) + other | 40 | 70 | 45 | 80 | 80 | 40 | | |
| | | | B-1 | 30 | 30 | 30 | 30 | 30 | 30 | | |
| | | | B-2 | 0 | 150 | 150 | 150 | 150 | 0 | | |
| | | Average particle diameter of filler (μm) | B-1 (Average primary particle diameter) | 0.02 | 0.04 | 0.04 | 0.02 | 0.02 | 0.02 | | |
| | | | B-1 (Average secondary particle diameter) | 10 | 40 | 40 | 10 | 10 | 10 | | |
| | | Consistency (mm) | Immediately after production | 14 | 13 | 15 | 14 | 14 | 14 | | |
| | Final paste | Composition added to intermediate paste (parts by mass) | (A) + other | 43.6 | 13.6 | 38.6 | 4.1 | 4.1 | 46.6 | 77.6 | 83.6 |
| | | | B-1 | 0 | 0 | 0 | 0 | 0 | 0 | 30 | 30 |
| | | | B-2 | 150 | 0 | 0 | 0 | 0 | 150 | 210 | 150 |
| | | Average particle diameter of filler (μm) | B-1 (Average primary particle diameter) | 0.02 | 0.04 | 0.04 | 0.02 | 0.02 | 0.02 | 0.04 | 0.016 |
| | | | B-1 (Average secondary particle diameter) | 0.5 | 1 | 1 | 0.5 | 1 | 0.5 | 0.5 | 100 |
| | | | B-2 (Average primary particle diameter) | 2.5 | 2.4 | 2.4 | 2.5 | 2.5 | 2.5 | 2.3 | 2.5 |
| | | | B-2 (Average secondary particle diameter) | 10 | 19 | 18 | 15 | 14 | 10 | 17 | 10 |
| Evaluation results | | Consistency (mm) | Immediately after production | 27.5 | 14 | 17 | 18 | 24 | 28 | 26 | 28 |
| | | | Two years at 25° C. | 22.1 | 19 | 22 | 18 | 29 | 25.5 | 29 | 11 |
| | | Runniness (mm) | Immediately after production | 0 | 0 | 0 | 0 | 0 | 0 | 0 | 0 |
| | | | Two years at 25° C. | 0 | 0 | 0 | 0 | 0 | 0 | 0 | 0 |
| | | Stringiness | Immediately after production | Good | Good | Good | Good | Good | Good | Good | Good |
| | | | Two years at 25° C. | Good | Good | Good | Good | Good | Good | Accept-able | Good |

TABLE 3

| | Ex. 14 | Ex. 15 | Ex. 16 | Ex. 17 | Ex. 18 | Ex. 19 | Ex. 20 | Com. Ex. 7 | Com. Ex. 8 |
|---|---|---|---|---|---|---|---|---|---|
| First agent | Ex. 1 | Ex. 2 | Ex. 3 | Ex. 4 | Ex. 5 | Ex. 6 | Ex. 7 | Com. Ex. 1 | Com. Ex. 3 |
| Second agent | Ex. 8 | Ex. 9 | Ex. 10 | Ex. 11 | Ex. 12 | Com. Ex. 5 | Ex. 13 | Com. Ex. 6 | Com. Ex. 6 |

TABLE 3-continued

| | | | Ex. 14 | Ex. 15 | Ex. 16 | Ex. 17 | Ex. 18 | Ex. 19 | Ex. 20 | Com. Ex. 7 | Com. Ex. 8 |
|---|---|---|---|---|---|---|---|---|---|---|---|
| Evaluation results (Kneaded product) | Consistency (mm) | Immediately after production | 25 | 25 | 28 | 26 | 31 | 24 | 26 | 25 | 26 |
| | | Two years at 25° C. | 29 | 27 | 32 | 30 | 34 | 25 | 29 | 41 | 49 |
| | Runniness (mm) | Immediately after production | 0 | 0 | 0 | 0 | 0 | 0 | 0 | 0 | 1 |
| | | Two years at 25° C. | 0 | 1 | 1.5 | 0 | 1 | 0 | 0 | 3 | 8 |
| | Stringiness | Immediately after production | Good | Good | Good | Good | Good | Good | Good | Accept-able | Accept-able |
| | | Two years at 25° C. | Good | Good | Good | Good | Good | Good | Good | Poor | Poor |
| | Discharge force (N) 0.9 mm guide tip | Immediately after production | 19 | | 35 | | 20 | 33 | 21 | 30 | 32 |
| | | Two years at 25° C. | 24 | | 49 | | 28 | 52 | 25 | 75 | 80 |
| | Flexural strength (MPa) | Immediately after production | 110 | 95 | 99 | 107 | 109 | 150 | 108 | 82 | 75 |
| | | Two years at 25° C. | 105 | 90 | 90 | 98 | 96 | 145 | 105 | 64 | 48 |
| | Marginal sealing | Immediately after production | Good | Good | Good | Good | Good | Good | Good | Good | Good |
| | | Two years at 25° C. | Good | Good | Good | Good | Good | Good | Good | Poor | Poor |

As shown in Tables 1 and 2, the paste-like compositions for dental use of the present invention showed small changes in consistency immediately after production and even after being stored at 25° C. for 2 years, and the runniness was desirable. No string was observed, and the stringiness was desirable even after 2-year storage at 25° C. The paste-like compositions for dental use of Examples 14 to 20 prepared as two-paste compositions were shown to excel in discharge force, flexural strength, and marginal sealing, in addition to having small consistency changes and desirable runniness and stringiness, as shown in Table 3, despite that factors involved in changes of paste extrudability and kneadability are more complex in two-paste compositions than in one-paste compositions, and stable paste properties are more difficult to achieve with two-paste compositions.

The invention claimed is:

1. A method for producing a paste-like composition for dental use that comprises a polymerizable monomer (A) and a filler (B), and in which the filler (B) comprises a particulate filler (B-1) having an average primary particle diameter of 0.001 to 0.2 μm, comprising:

mixing the polymerizable monomer (A) and the particulate filler (B-1) having an average primary particle diameter of 0.001 to 0.2 μm to obtain an intermediate paste; and additionally mixing the polymerizable monomer (A) with the intermediate paste to obtain a final paste as the paste-like composition for dental use, the particulate filler (B-1) being mixed in an amount of 30 to 150 parts by mass relative to total 100 parts by mass of a total amount of polymerizable monomer (A) in obtaining the intermediate paste, wherein:

polymerizable monomer (A) is at least one of a polymerizable monomer having a phosphoric acid group, a polymerizable monomer having a sulfonic acid group, a polymerizable monomer having a carboxylic acid group, a hydrophobic monofunctional polymerizable monomer having no acidic group, an aromatic bifunctional polymerizable monomer having no acidic group, an aliphatic bifunctional polymerizable monomer having no acidic group, and a tri- or higher-functional polymerizable monomer having no acidic group;

the particulate filler (B-1) is not added to the intermediate paste during said additionally mixing to obtain the final paste;

the final paste has a consistency of 15 to 40 mm;

the particulate filler (B-1) contained in the final paste has an average secondary particle diameter of 20 μm or less;

the intermediate paste has a consistency of 5 to 20 mm; and a content of polymerizable monomer (A) is 5 to 60 parts by mass relative to a total 100 parts by mass of the paste-like composition for dental use.

2. The method for producing a paste-like composition for dental use according to claim 1, wherein the particulate filler (B-1) contained in the final paste has an average secondary particle diameter of 10 μm or less.

3. The method for producing a paste-like composition for dental use according to claim 2, wherein the intermediate paste has a consistency of 10 to 16 mm.

4. The method for producing a paste-like composition for dental use according to claim 1, wherein the particulate filler (B-1) contained in the intermediate paste has an average secondary particle diameter of 100 μm or less.

5. The method for producing a paste-like composition for dental use according to claim 1, wherein the paste-like composition for dental use further comprises a filler (B-2) having an average primary particle diameter of more than 0.2 μm and 30 μm or less.

6. The method for producing a paste-like composition for dental use according to claim 5, wherein the filler (B-2) is mixed when obtaining the intermediate paste.

7. The method for producing a paste-like composition for dental use according to claim 5, wherein the filler (B-2) is mixed when obtaining the final paste.

8. The method for producing a paste-like composition for dental use according to claim 1, wherein the particulate filler (B-1) contained in the final paste has an average secondary particle diameter of 5 μm or less.

9. The method for producing a paste-like composition for dental use according to claim 8, wherein the paste-like composition for dental use further comprises a filler (B-2) having an average primary particle diameter of more than 0.2 μm and 30 μm or less.

10. The method for producing a paste-like composition for dental use according to claim 9, wherein the filler (B-2) is mixed when obtaining the intermediate paste.

11. The method for producing a paste-like composition for dental use according to claim 9, wherein the filler (B-2) is mixed when obtaining the final paste.

* * * * *